(12) United States Patent
Dziedzic et al.

(10) Patent No.: US 8,685,029 B2
(45) Date of Patent: Apr. 1, 2014

(54) ROD REDUCTION INSTRUMENT AND METHODS OF ROD REDUCTION

(75) Inventors: Sara Dziedzic, Raynham, MA (US); James Donahue, Raynham, MA (US); Glen Presbrey, Raynham, MA (US)

(73) Assignee: DePuy Synthes Products, LLC, Raynham, MA (US)

( * ) Notice: Subject to any disclaimer, the term of this patent is extended or adjusted under 35 U.S.C. 154(b) by 212 days.

(21) Appl. No.: 13/245,076

(22) Filed: Sep. 26, 2011

(65) Prior Publication Data

US 2012/0078308 A1 Mar. 29, 2012

Related U.S. Application Data

(60) Provisional application No. 61/386,724, filed on Sep. 27, 2010.

(51) Int. Cl.
*A61B 17/70* (2006.01)

(52) U.S. Cl.
USPC .......................................... 606/86 A; 606/99

(58) Field of Classification Search
CPC .................................................. A61B 17/7076
USPC .................................................. 606/86 A, 99
See application file for complete search history.

(56) References Cited

U.S. PATENT DOCUMENTS

| | | | |
|---|---|---|---|
| 4,700,926 A * | 10/1987 | Hansen | 251/149.8 |
| 5,020,519 A | 6/1991 | Hayes | |
| 5,616,143 A | 4/1997 | Schlapfer | |
| 5,720,751 A * | 2/1998 | Jackson | 606/86 R |
| 6,036,692 A | 3/2000 | Burel | |
| 6,440,133 B1 * | 8/2002 | Beale et al. | 606/86 A |
| 6,743,231 B1 | 6/2004 | Gray | |
| 6,746,449 B2 | 6/2004 | Jones | |
| 6,755,829 B1 | 6/2004 | Bono | |
| 7,179,261 B2 | 2/2007 | Sicvol | |
| 7,320,689 B2 | 1/2008 | Keller | |
| 7,462,182 B2 | 12/2008 | Lim | |
| 7,481,813 B1 | 1/2009 | Purcell | |
| 7,491,207 B2 | 2/2009 | Keyer | |
| 7,608,081 B2 | 10/2009 | Abdelgany | |
| 7,611,517 B2 | 11/2009 | Lim | |
| 7,618,444 B2 | 11/2009 | Shluzas | |
| 7,744,598 B2 | 6/2010 | Brumfield | |
| 7,749,233 B2 | 7/2010 | Farr | |
| 7,771,430 B2 | 8/2010 | Jones | |
| 7,776,040 B2 | 8/2010 | Markworth | |
| 7,799,031 B2 | 9/2010 | Miller | |

(Continued)

FOREIGN PATENT DOCUMENTS

| | | |
|---|---|---|
| WO | WO 2009152302 | 12/2009 |
| WO | WO 2009152308 | 12/2009 |

*Primary Examiner* — Ellen C Hammond

(57) ABSTRACT

An instrument for reducing a spinal rod includes a reduction member sized and shaped to be positioned about an anchor extension connected to a bone anchor, an actuator assembly connected to the reduction member and operable to move the reduction member distally relative to the anchor extension along a longitudinal axis of the anchor extension, and a connection mechanism for removable and replaceable connection of the actuator assembly to a proximal end of the anchor extension. The connection mechanism is adjustable between a first position in which the connection mechanism connects the actuator assembly to the proximal end of the anchor extension and a second position in which the connection mechanism and the actuator assembly are released from the anchor extension.

25 Claims, 12 Drawing Sheets

(56) References Cited

U.S. PATENT DOCUMENTS

| | | | |
|---|---|---|---|
| 8,192,438 B2* | 6/2012 | Garamszegi | 606/86 A |
| 2004/0254576 A1 | 12/2004 | Dunbar | |
| 2006/0036260 A1* | 2/2006 | Runco et al. | 606/99 |
| 2006/0111712 A1 | 5/2006 | Jackson | |
| 2006/0200132 A1 | 9/2006 | Chao | |
| 2007/0213722 A1 | 9/2007 | Jones | |
| 2007/0260261 A1* | 11/2007 | Runco et al. | 606/104 |
| 2007/0282337 A1 | 12/2007 | Garamszegi | |
| 2008/0015601 A1 | 1/2008 | Castro | |
| 2008/0077134 A1 | 3/2008 | Dziedzic | |
| 2008/0077135 A1 | 3/2008 | Stad | |
| 2008/0119849 A1 | 5/2008 | Beardsley | |
| 2008/0154277 A1 | 6/2008 | Machalk | |
| 2008/0154280 A1 | 6/2008 | Schumacher | |
| 2008/0172062 A1 | 7/2008 | Donahue | |
| 2008/0177269 A1 | 7/2008 | Seelig | |
| 2008/0234678 A1 | 9/2008 | Gutierrez | |
| 2008/0300638 A1 | 12/2008 | Beardsley | |
| 2008/0312703 A1 | 12/2008 | Hestad | |
| 2009/0030419 A1* | 1/2009 | Runco et al. | 606/99 |
| 2009/0143828 A1 | 6/2009 | Stad | |
| 2009/0157125 A1 | 6/2009 | Hoffman | |
| 2009/0163962 A1 | 6/2009 | Dauster | |
| 2009/0228052 A1 | 9/2009 | Beardsley | |
| 2009/0228054 A1 | 9/2009 | Hoffman | |
| 2009/0228055 A1 | 9/2009 | Jackson | |
| 2009/0281582 A1 | 11/2009 | Villa | |
| 2010/0069972 A1 | 3/2010 | Jones | |
| 2010/0121385 A1 | 5/2010 | Blain | |
| 2010/0121386 A1 | 5/2010 | Peultier | |
| 2010/0137875 A1 | 6/2010 | Marino | |
| 2010/0185248 A1 | 7/2010 | Barry | |
| 2010/0228302 A1 | 9/2010 | Dauster | |

* cited by examiner

ROD REDUCTION INSTRUMENT AND METHODS OF ROD REDUCTION

CONTINUING DATA

This application claims the benefit of U.S. Provisional Application No. 61/386,724, filed Sep. 27, 2010, which is hereby incorporated by reference in its entirety.

BACKGROUND

Spinal fixation elements are used in orthopedic surgery to align and/or fix a desired special relationship between the vertebrae of the spine. Such spinal fixation elements, such as, for example, a rigid or dynamic spinal rod, may be coupled to multiple vertebrae by attaching the spinal fixation element to bone anchors, such as hooks, bolts, wires, or screws, anchored in the vertebrae. Once installed, the spinal fixation element may hold the vertebrae in a desired spatial relationship to, for example, provide stability to the spine or to fix the vertebrae until desired healing or spinal fusion has taken place.

While current spinal fixation systems have proven effective, difficulties have been encountered in mounting spinal rods into the rod receiving member of the respective bone anchors. In particular, it can be difficult to align and seat the rod into the rod receiving portion of the bone anchors due to the positioning and rigidity of the vertebrae. Thus, the use of a spinal rod reduction instrument, also sometimes referred to as a spinal rod approximator or persuader, is often required in order to grasp the bone anchor and reduce the spinal rod into the rod-receiving member of the bone anchor.

While several rod reduction instruments are known in the art, some tend to be difficult and time-consuming to use. Accordingly, there is a need for improved instruments and methods for reducing a spinal rod, or other spinal fixation element, relative to one or more bone anchors.

SUMMARY

Disclosed herein are improved instruments and methods for reducing a spinal rod relative to a bone anchor connected to an anchor extension. In accordance with one aspect, an instrument for reducing a spinal rod relative to a bone anchor connected to an anchor extension includes a reduction member sized and shaped to be positioned about the anchor extension, an actuator assembly connected to the reduction member and operable to move the reduction member distally relative to the anchor extension along a longitudinal axis of the anchor extension, and a connection mechanism for removable and replaceable connection of the actuator assembly to a proximal end of the anchor extension. The connection mechanism is adjustable between a first position in which the connection mechanism connects the actuator assembly to the proximal end of the anchor extension and a second position in which the connection mechanism and the actuator assembly are released from the anchor extension, Upon connection of the actuator assembly to the anchor extension by the connection mechanism, operation of the actuator assembly moves the reduction member distally to engage and move a spinal rod into a U-shaped slot of a rod receiver member of the bone anchor.

BRIEF DESCRIPTION OF THE FIGURES

These and other features and advantages of the instruments and methods disclosed herein will be more fully understood by reference to the following detailed description in conjunction with the attached drawings in which like reference numerals refer to like elements through the different views. The drawings illustrate principles of the instruments and methods disclosed herein and, although not to scale, show relative dimensions.

DETAIL DESCRIPTION OF EXEMPLARY EMBODIMENTS

Certain exemplary embodiments will now be described to provide an overall understanding of the principles of the structure, function, manufacture, and use of the instruments and methods disclosed herein. One or more examples of these embodiments are illustrated in the accompanying drawings. Those of ordinary skill in the art will understand that the instruments and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The articles "a" and "an" are used herein to refer to one or to more than one (i.e. to at least one) of the grammatical object of the article. By way of example, "an element" means one element or more than one element.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

Figure 1:
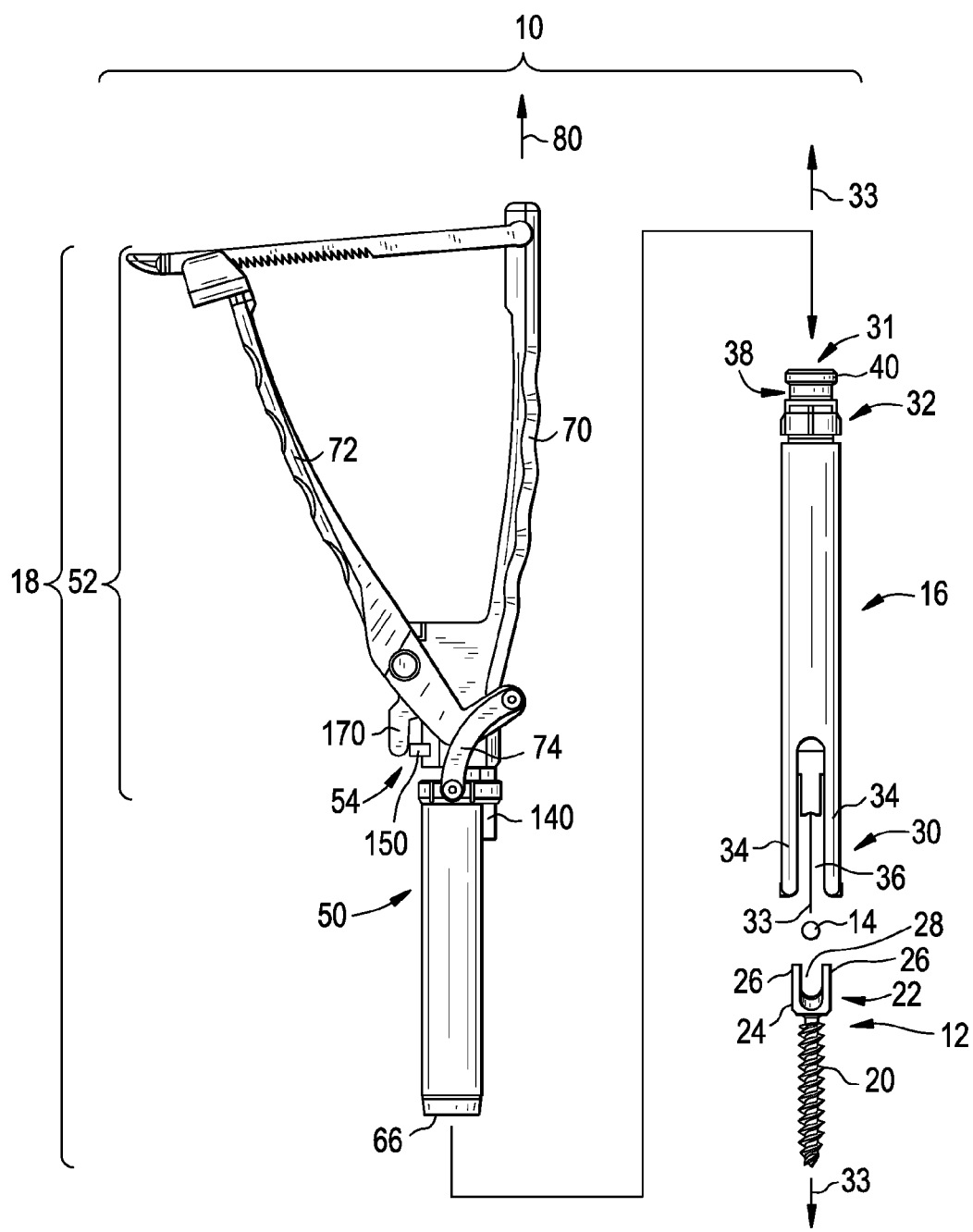
FIG. 1 is an exploded view of an exemplary spinal system including a bone anchor, a spinal rod, an anchor extension, and an instrument for reducing the spinal rod relative to the bone anchor.

FIG. 1 illustrates an exemplary embodiment of a spinal system 10 including a bone anchor 12, a spinal rod 14, an anchor extension 16, and a spinal rod reduction instrument 18. The components of the system 10 will be described in more detail below.

The exemplary spinal system 10 may include multiple bone anchors 12 of various types and sizes suitable for implantation into the vertebrae of the spine. Such bone anchors 12 may include bone screws, hooks, and bolts. In the illustrated embodiment, the exemplary bone anchor 12 includes a bone screw 20 having one or more bone engaging threads and a rod receiving member 22 connected to the bone screw 20. The rod receiving member 22 of the exemplary bone anchor 12 has a distal base 24 and two spaced apart arms 26 extending proximally from the base 24 and forming a U-shaped slot 28 for receiving one of the spinal rods 14 of the system 10. The exemplary bone anchor 12 is a polyaxial bone screw designed for posterior implantation through the pedicle or lateral mass of a vertebra. In addition, the spinal system 10 may include additional bone anchors of various types and sizes including, for example, one or more mobile or dynamic screws, monoaxial screws, favored angle screws or uniplanar screws all of varying sizes.

The bone screw 20 of the exemplary bone anchor 12 may be cannulated, having a central passage or cannula extending the length of the bone screw 20 to facilitate delivery of the bone anchor 12 over a guide wire in, for example, minimally invasive procedures. The bone screw 20 may also include one or more side wall openings or fenestrations that communicate with the cannula to permit bone in-growth or to permit the dispensing of bone cement or other materials through the bone anchor 12. The bone anchor 12 may also include a closure mechanism that is positionable between and may engage the arms 26 to capture a spinal rod 14 within the receiver member 22 and fix the spinal rod 14 with respect to the receiver member 22. The closure mechanism in the exemplary embodiment is an internal set screw (not shown) having an external thread that engages the internal thread of the receiver member to capture a spinal fixation element within the slot 28 of the receiver member and, when fully tightened, to fix the spinal rod 14 relative to the receiver member 22. Alternatively, the closure mechanism may be dual closure mechanism having an inner and an outer set screw, such as, for example, the Expedium Dual Innie Polyaxial Screw available from DePuy Spine, Inc. of Raynham, Mass. In addition, the closure mechanism may be a non-threaded twist in cap, such as, for example, the Monarch Typhoon Cap available from DePuy Spine, Inc. of Raynham, Mass., and described in U.S. Pat. No. 6,755,829, incorporated herein by reference.

The distal base 24 of the receiver member 22 is generally cylindrical in shape and includes a distal end surface which is generally annular in shape defining a circular opening through which at least a portion of the bone screw 20 extends. Each arm 26 of the receiver member 22 extends proximally from the base 24 of the receiver member 22 to a free end. The outer surface of each arm 26 may include a feature, such as a recess, dimple, groove, notch, projection, or the like, to facilitate connection of the receiver member 22 and, thus, the bone anchor 12, to instruments, including, for example, the anchor extension 16. For example, the outer surface of each arm 26 may include an arcuate groove at the respective free end of the arms. Such grooves are described in more detail in U.S. Pat. No. 7,179,261, which is incorporated herein by reference.

The exemplary spinal system 10 may include multiple spinal rods 14 that may be connected to the bone anchors of the system to thereby create a spinal construct that interconnects multiple vertebrae. The spinal rods of the system may have varying lengths, diameters, shapes (e.g., straight or curved), and cross-sections. The spinal rods may be constructed from titanium, titanium alloys, stainless steel, cobalt chrome, PEEK, or other materials suitable for rigid fixation. Alternatively, the spinal rod may be a dynamic stabilization member that allows controlled mobility between the instrumented vertebrae.

Continuing to refer to FIG. 1, one or more anchor extensions 16 may be provided in the system 10 for connection to the bone anchors in the system. The anchor extensions 16 may be provided in various sizes and shapes depending on the application of the anchor extension. For example, anchor extensions may be utilized to manipulate the respective bone anchor and vertebrae in which the bone anchor is implanted, to deliver additional implants or instruments to the bone anchor or the vertebra, or to facilitate minimally invasive surgical procedures. Exemplary anchor extensions include the EXPEDIUM Vertebral Body Derotation Instruments and the VIPER and VIPER 2 Screw Extensions available from DePuy Spine, Inc. of Raynham, Mass. Exemplary anchors extensions are described in the following patents and patent applications: U.S. Patent Application Publication Nos. 2006/0200132, 2008/0172062, 2008/0077134, 2008/0077135, and 2009/0143828 and U.S. Pat. No. 7,179,261. Each of the foregoing patents and patent applications is hereby incorporated herein by reference.

The exemplary anchor extension 16 includes a distal end 30 configured for connection to a bone anchor, such as bone anchor 12, a proximal end 32, and a longitudinal axis 33 extending between the proximal end 32 and the distal end 30 of the anchor extension 16. The exemplary anchor extension 16 is a generally cylindrical sleeve having a distal end 30 that is preferably connectable to the proximal receiver member 22 of the bone anchor 12. The anchor extension 16 includes a central passage 31 opening at the proximal end 32 and extending to an opening at the distal end 34. The central passage 31 may be used to deliver instruments and implants to the bone anchor 12. The distal end 30 of the anchor extension 16 may include a pair diametrically opposed, spaced apart fingers 34 that define a pair of opposed longitudinal slots 36 for receiving the spinal rod 14 during minimally invasive procedures or vertebral body derotation or manipulation procedures. Each slot 36 communicates with the central passage 31 and is open at the distal end 30 of the anchor extension 16 and extends proximally from the distal end 30 of the anchor extension 16 in an orientation parallel to the longitudinal axis 33. The inner surface of each finger 34, preferably at the distal end of the finger, may include one or more feature, such as, for example, a recess, dimple, groove, notch, projection, or the like, for engaging a complimentary feature on one the outer surface of one of the arms 26 of the bone anchor 12. In one embodiment, for example, the feature on the inner surface of each finger 34 may be an arcuate projection for engaging a corresponding arcuate groove on the outer surface of each arm 22 of the bone anchor 12.

The proximal end 32 of the anchor extension 16 may include one or more feature, such as, for example, a recess, groove, dimple, notch, projection, or the like, for engaging a complimentary feature on a secondary instrument, such as the spinal rod reduction instrument 18, to facilitate connection of the secondary instrument to the anchor extension 16. In the exemplary embodiment, for example the proximal end 38 of the anchor extension 16 includes a groove 38 about the circumference of the outer surface of the proximal end 32 of the anchor extension 16. A flange 40 formed on the proximal end 32 of the anchor extension 16 provides the proximal end surface or wall of the groove 38. The flange 40 inhibits axial motion of a secondary instrument, such as instrument 18, connected to the anchor extension 16 in a proximal direction along the longitudinal axis 33 of the anchor extension 16.

Continuing to refer to FIG. 1 and also referring to FIGS. 2-6, the exemplary spinal rod reduction instrument 18 includes a reduction member 50, an actuator assembly 52, and a connection mechanism 54. The reduction member 50 may be positioned about the anchor extension 16 and may be movable axially along the longitudinal axis 33 of the anchor extension 16. The actuator assembly 52 may be connected to the reduction member 50 and may be operable to move the reduction member 50 distally relative to the anchor extension 16 along the longitudinal axis 33 of the anchor extension 16. The connection mechanism 54 permits removable and replaceable connection of the actuator assembly 52 to the proximal end 32 of the anchor extension 16. As described in more detail below, the connection mechanism 54 is adjustable between a first position in which the connection mechanism 52 connects the actuator assembly 52 to the proximal end 32 of the anchor extension 16 and a second position in which the connection mechanism 54 and the actuator assembly 52 are released from the anchor extension 16. Upon connection of the actuator assembly 52 to the anchor extension 16 by the connection mechanism 54, operation of the actuator assembly 52 moves the reduction member 50 distally to engage and move a spinal rod 14 into the U-shaped slot 28 of the receiver member 22 of the bone anchor 12.

The reduction member 50 of the exemplary instrument 18 may be a cylindrical sleeve having a proximal end 62 and a distal end 64 having a central passage opening at the proximal end 62 and extending to an opening at the distal end. The diameter of the central passage is greater than the outer diameter of the anchor extension 16 to permit linear, reciprocal movement of the reduction member 50 relative to the anchor extension 16. The reduction member 50 may be shaped other than cylindrical, including shapes that permit engagement with the actuator assembly 52 at the proximal end 62, engagement of the spinal rod 14 at the distal end 64, and axial motion of the reduction member 50 relative to the spinal rod 14. In the exemplary embodiment, the distal end 64 has an annular rod engagement surface 66 for engaging the spinal rod 14 during the rod reduction process. In certain alternative embodiments, the rod engagement surface 66 may include a first pair of diametrically opposed arcuate cut-outs having a size and shape corresponding to spinal rod. In other alternative embodiments, the rod engagement surface 66 may include a second pair of diametrically opposed arcuate cut-outs each of the is offset 90 degrees from one of the cut-outs of the first pair. In the illustrated embodiment of the instrument 18, the rod engagement surface 66 lacks arcuate cut-outs for engaging the rod which permits the reduction member 50 to positioned in any rotational orientation relative to the anchor extension 16 and the spinal rod 14.

The actuator assembly 52 of the exemplary instrument 18 includes a first handle 70, a second handle 72 pivotally connected to the first handle 70, and a linkage 74 connecting the second handle 72 to the reduction member 50. Pivoting of the second handle 72 toward the first handle 70 causes the reduction member 50 to move distally and thereby reduce the spinal rod 14 relative to the bone anchor 12. The first handle 70 includes a distal base 76 and handle portion 78 that extends proximally from the distal base 76 along an axis 80 oriented generally parallel to the longitudinal axis 33 of the anchor extension 16. The distal base 76 of the first handle 70 includes a central passage 82 through the base 76 that aligns with the central passage of the reduction member 50 and the central passage 31 of the anchor extension 16 when the instrument 18 is connected to the anchor extension 16. The distal base 76 further includes two spaced apart flanges 84 each having an opening for receiving a pivot pin 88 that connects the second handle 72 to the first handle 70.

Figure 4:
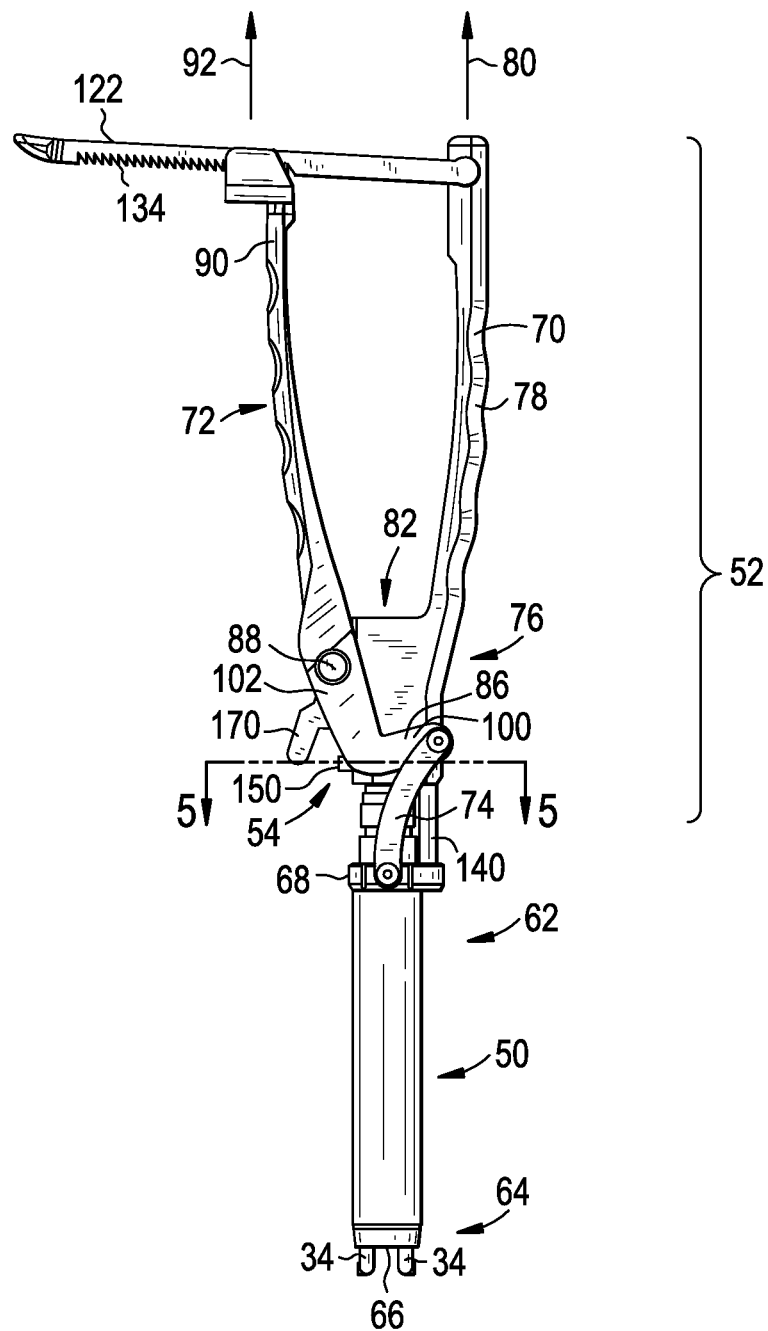
FIG. 4 is a side view of the instrument of the system of FIG. 1, illustrating the instrument connected to the anchor extension of the system and the reduction member of the instrument in a distal position.

The second handle 72 has a forked distal end including two spaced-apart arms 86 and a handle portion 90 that extends proximally from the arms 86 along an axis 92 oriented generally parallel to the longitudinal axis 33 of the anchor extension 16 and parallel to the handle axis 80 of the handle portion 78 of the first handle 70 depending on the pivot position of the second handle 72 (e.g., FIG. 4). Each distal arm 86 of the second handle 72 is generally L-shaped and includes a base member 100 that extends generally perpendicular to an elongated member 102. The elongated member 102 of each arm 86 includes a first opening 94 for receiving the pivot pin 88. The base member 100 of each arm 86 includes a second opening 96 for receiving one of the linkage pins 98. When assembled, the first opening 94 and the pivot pin 88 are positioned on one side of the central passage 82 of the distal base 76 and the second opening 96 and the linkage pin 98 received therein are positioned on the other side of the central passage 82.

The linkage 74 of the handle assembly 18 includes a pair of opposing linkage members 104, each one of which connects one of the arms 86 of the distal end of the second handle 72 to the proximal end 62 of the reduction member 50. Each linkage member 104 includes a first end 106 having an opening 108 for receiving a linkage pin 98 to connect the linkage member 104 to one of the arms 86 of the distal end of the second handle 72 and a second end 112 having an opening 113 for receiving a linkage pin 98 to connect the linkage member 104 to the proximal end 62 of the reduction member 50. Diametrically opposed openings 114 are provided on the proximal end 62 of the reduction member 50 to receive linkage pins 98 connecting the second ends 110 of each linkage member 104 to the collar 68 of the reduction member 50. The linkage members 104 are each generally arcuate in shape, although other shapes may be utilized to translate the motion of handles 70, 72 to the reduction member 50. Likewise, the linkage 74 may include additional linkage members to translate the motion of handles 70, 72 to the reduction member 50 depending on, for example, the force desired to be transmitted to reduction member 50.

A spring 120, such as, for example, a torsion spring, may be positioned between the first handle 70 and the second handle 72 to bias the second handle 72 away from the first handle 70. A ratchet arm 122 may be provided to hold the position of the second handle 72 relative to the first handle 70. In the exemplary embodiment, the ratchet arm 122 is pivotally connected at a first end 124 to the proximal end of the handle portion 78 of the first handle 70 to permit the ratchet arm 122 to pivot into and out engagement with the proximal end of the handle portion 90 of the second handle 72. A spring 126 biases the head of a pin 128 into contact with the hinge pin 130 formed on the first end 124 of the ratchet arm 122 to provide a drag force on the hinge pin 120. Retaining pin 132 engages the end of the hinge pin 130 to connect the ratchet arm 122 to the first handle 70. The ratchet arm 122 includes a toothed rack 134 for engagement with a pawl 136 that collectively permit motion of the second handle 72 toward the first handle 70 while inhibiting motion of the second handle 72 away from the first handle 70.

In the exemplary embodiment illustrated in FIGS. 1-8, the first handle 70 and the second handle 72 are connected to the reduction member 50 through linkage 74 and distal base 76 engages a collar 68 provided at the proximal end 62 of the reduction member 50. The actuator assembly 52 may include an alignment member connecting the actuator assembly 52 to the reduction member 50 and preventing rotation of the actuator assembly 52 relative to the reduction member 50. In the exemplary embodiment, the alignment member is a cylindrical post 140 extending distally from the distal base 76 of the first handle 70 to engage an opening 142 provided in the collar 68 of the reduction member 50. When the post 140 is seated in the opening 142 of the collar 68, the actuator assembly 52 is inhibited from rotation relative to the reduction member 50 during operation of the actuator assembly 52.

Figure 12:
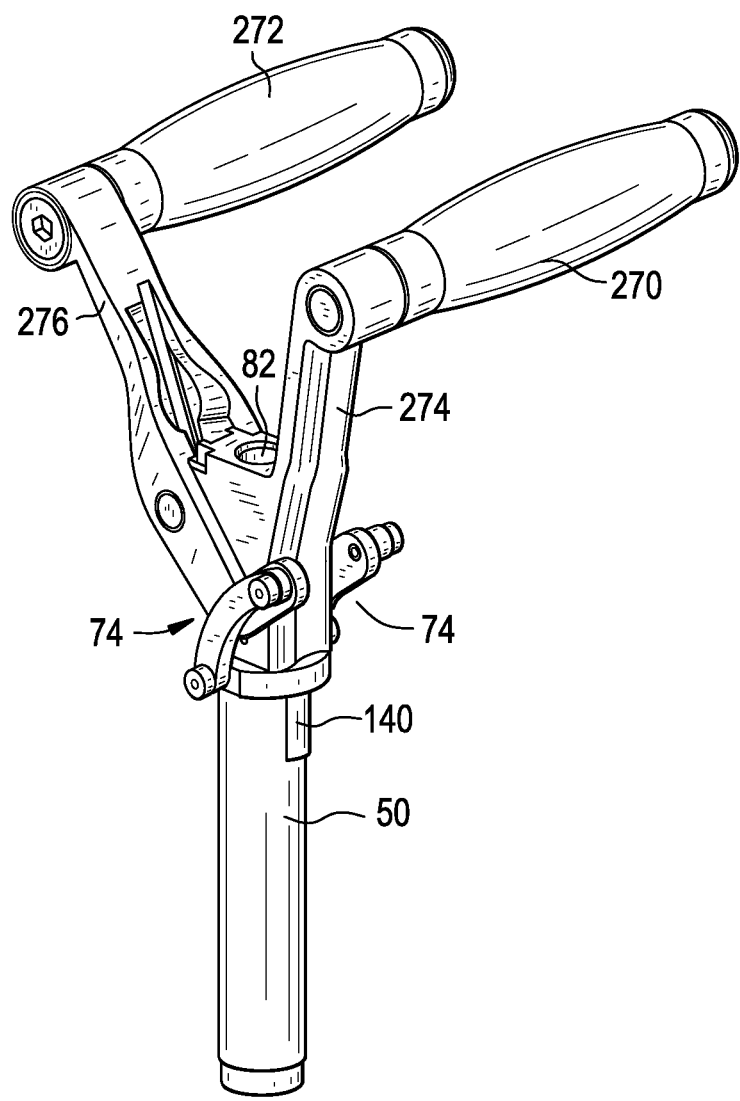
FIG. 12 is perspective view of another embodiment of an instrument for reducing a spinal rod.

In the exemplary embodiment, the first handle 70 is fixed relative to the reduction member 50 and the anchor extension 16 and the second handle 72 pivots relative to the first handle 70 to move the reduction member 50. In alternative embodiments, the first handle 70 and the second handle 70 both may pivot relative to each other. In further alternative embodiments, a portion or all of the first handle 70 and the second handle 72 may be oriented generally perpendicular to longitudinal axis 33 of the anchor extension. FIG. 12 illustrates an exemplary embodiment of an instrument for reducing a spinal rod in which the proximal portion 270 of the first handle 70 is oriented generally perpendicular to the distal portion 274 of the first handle 70 and the proximal portion 272 of the second handle 72 is oriented generally perpendicular to the distal portion 276 of the second handle 72. In still further alternative embodiments, the first handle 70, second handle 72, and linkage 74 may be replaced with other mechanisms for imparting linear motion to the reduction member 50, such mechanisms preferable providing mechanical advantage during operation. For example, the actuator assembly 52 may include a threaded mechanism that employs a threaded member, the rotation of which advances the reduction member 50 distally.

Refer to FIGS. 2-6, the connection mechanism 54 operates to permit removable and replaceable connection of the actuator assembly 52 to the proximal end 32 of the anchor extension 16. In the exemplary embodiment, the connection mechanism 54 includes a collar 150 having a slot 152 that is sized and shaped for positioning about the proximal end 32 of the anchor extension 16. In the exemplary embodiment, the collar 150 is positioned about the groove 38 provided on the proximal end 32 of the anchor extension 16. The slot 152 has first end 154 with a reduced width $W_1$ and a second end 156 with an increased width $W_2$. The reduced width $W_1$ of the first end 154 of the slot 152 is preferably less than the diameter D of the flange 40 provided on the proximal end 32 of the anchor extension 16 and the increased width $W_2$ of the second end 156 of the slot 152 is greater than the diameter D of the flange 40 to permit removal of the collar 150 from the anchor extension 16.

Figure 2:
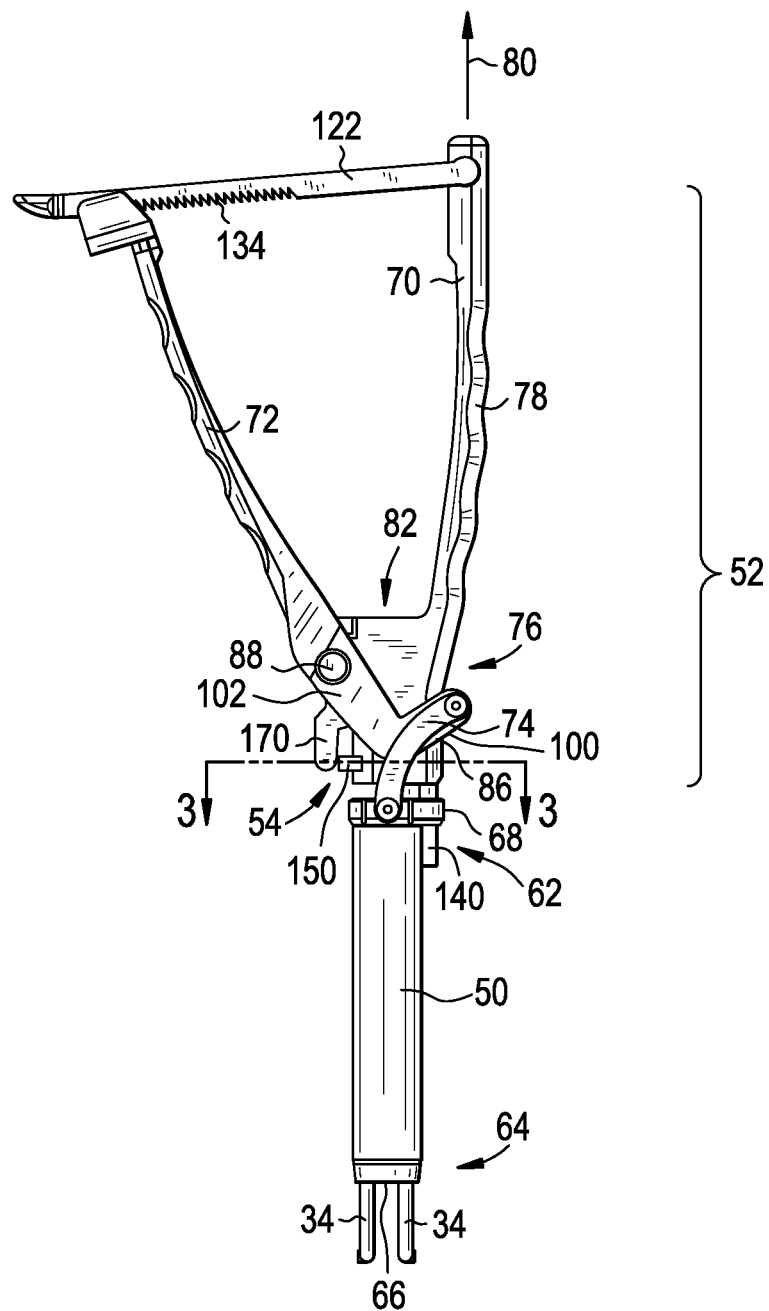
FIG. 2 is a side view of the instrument of the system of FIG. 1, illustrating the instrument connected to the anchor extension of the system and the reduction member of the instrument in a proximal position.
Figure 3:
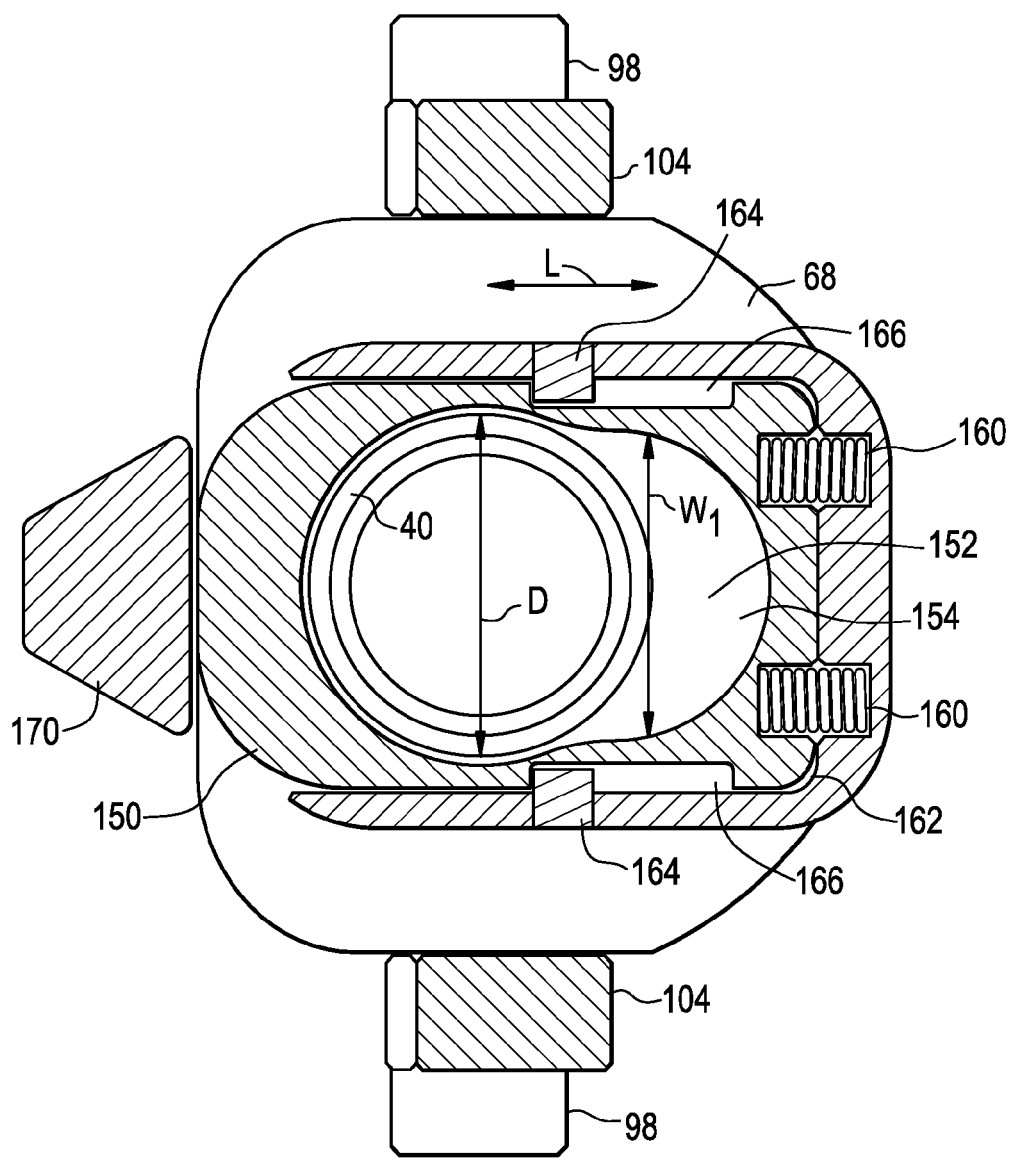
FIG. 3 is a cross sectional view along the line 3-3 in FIG. 2 of the connection mechanism of the spinal instrument of FIG. 2, illustrating the collar of the connection mechanism in a released position.
Figure 5:
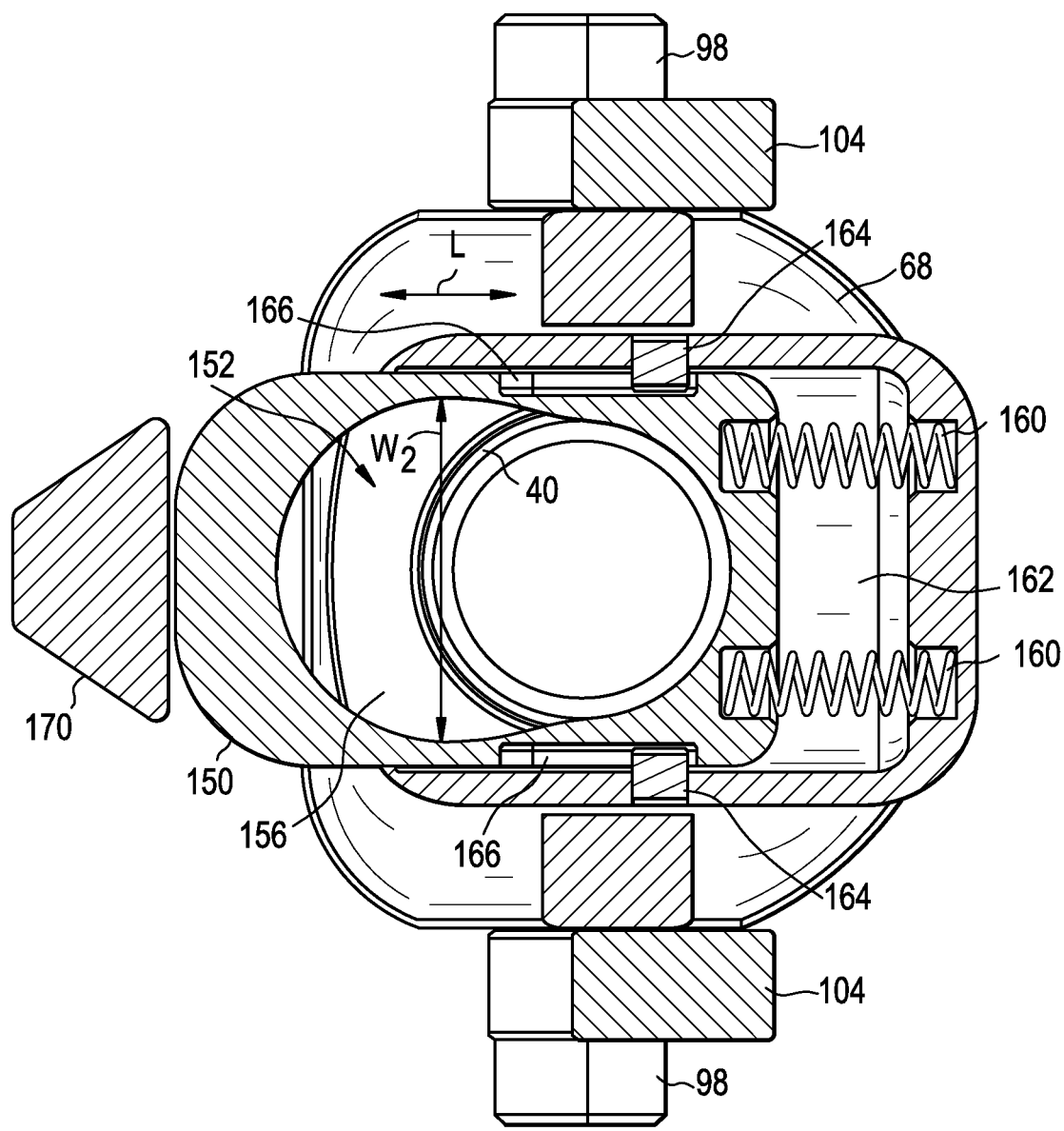
FIG. 5 is a cross sectional view along the line 5-5 in FIG. 4 of the connection mechanism of the spinal instrument of FIG. 4, illustrating the collar of the connection mechanism in a connected position.
Figure 6:
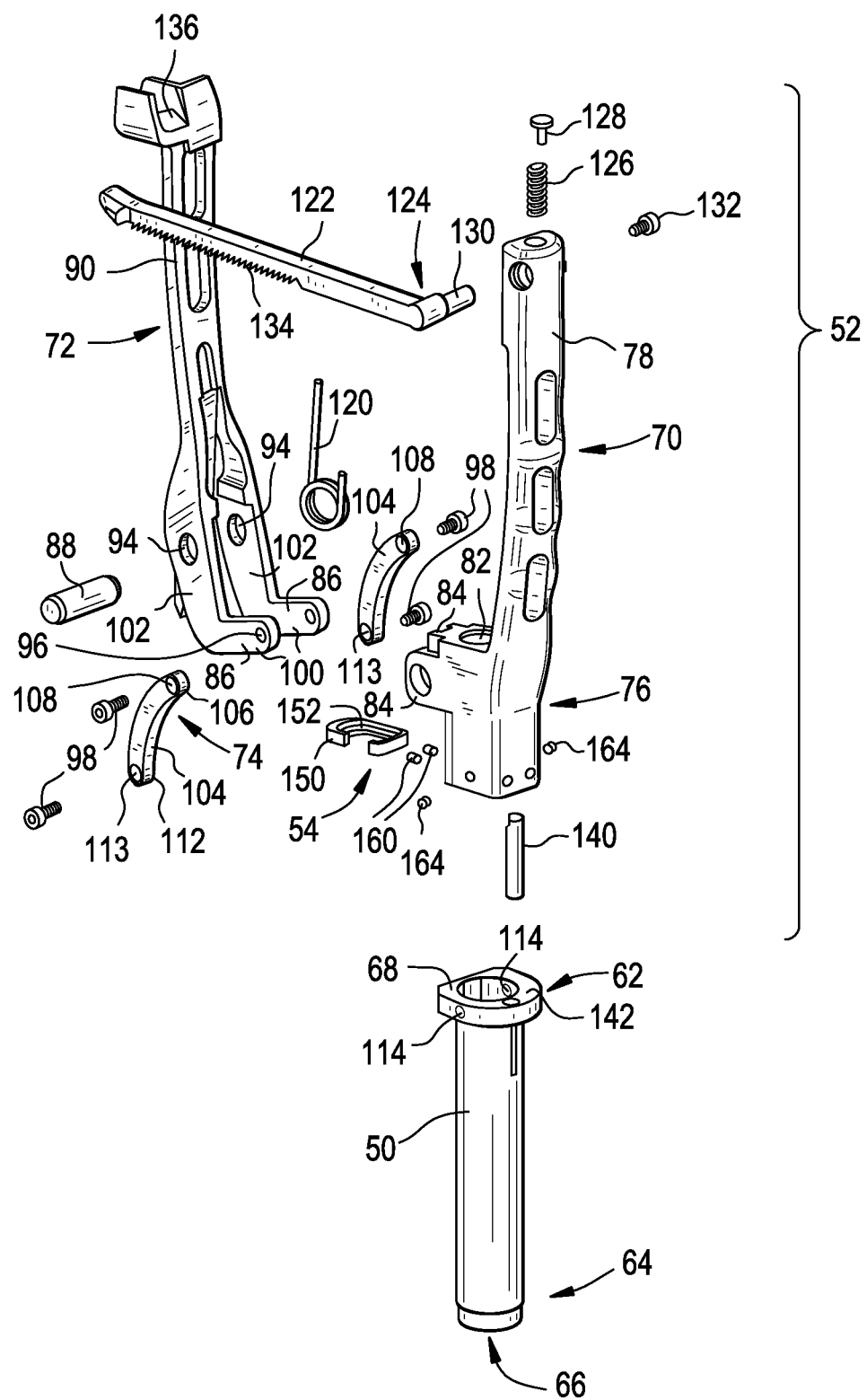
FIG. 6 is an exploded view of the spinal instrument of system of FIG. 1.

The collar 150 is linearly adjustable, along the line L, transverse to the longitudinal axis 33 of the anchor extension 16 to move the collar 150 between a first, connected position, illustrated in FIGS. 4 and 5, in which the first end 154 of the slot 152 is centered about the groove 38 provided on the proximal end 32 of the anchor extension 16 to connect the actuator assembly 52 to the proximal end 32 of the anchor extension 16 and a second, released position, illustrated in FIGS. 2 and 3, in which the second end 156 of the slot 152 is centered about the groove 38 to permit removal of the connection mechanism 54 and the actuator assembly 52 from the anchor extension 16. In the first position, the first end 154 of the slot 152 is positioned distal to the flange 40 and during operation of the actuator assembly 52 the collar 150 engages the flange 40 to inhibit movement of the collar 150 proximally along the longitudinal axis 33 of the anchor extension 16. In the second position, the collar 150 may be moved proximally over the flange 40 to remove the collar 150 and, thus, the actuator assembly 52 from the anchor extension 16.

In the exemplary embodiment, the collar 150 is positioned within an open sided chamber 162 formed the distal base 76 of the first handle 70. The collar 150 may be biased to either the first position or the second position. In the embodiment, for example, the collar 150 is biased to the first position by a pair of springs 160 and retention pins 164 engage slots 166 in the collar 150 to retain the collar 150 in the chamber 162. In certain embodiments, operation of the actuator assembly 52 may cause the collar 150 to move to the first position or the second position. In the exemplary embodiment, for example, operation of the actuator assembly 52 by movement of the second handle 72 toward the first handle 70 causes the collar 150 to move to the first position thereby connecting the actuator assembly 52 to the anchor extension 16. An engagement member 170 connected to one or both of the arms 86 of the distal end of the second handle 72 engages the collar 150 to move the collar 150 depending on the position of the second handle 72. In the exemplary embodiment, the engagement member 170 engages the collar 150 distal to the pivot axis of the second handle 72 as defined by pivot pin 84 and, thus, when the second handle 72 is spaced-apart from the first handle 70, as illustrated in FIG. 2, the collar 150 is moved to the second position, illustrated in FIG. 3. Movement of the second handle 72 toward the first handle 70, as illustrated in FIG. 4, causes engagement member 170 to move away from the collar 150 allowing collar 150 to move to the first position, illustrated in FIG. 5, under the biasing force of the springs 160.

In alternative embodiments, the collar 150 may be connected to the engagement member 170 or to another portion of the handles 70 and 72. For example, the collar 150 may be pivotally connected to the engagement member 170 such that movement of the second handle 72 also causes movement of the collar 150 between the first and second positions. In another exemplary embodiment, the free end of the engagement member 170 may be positioned within a slot or other opening provided in the collar 150 to connect the second handle 72 to the collar 150. In another exemplary embodiment, the collar member 150 may be connected to the second handle 72 and may be positioned proximal to the pivot pin 88 such that movement of the second handle 72 toward the first handle 70 causing the collar 150 to move to the first, connected position.

In alternative embodiments, the collar 150 may be movable between the first position and the second position independent of the operation of the actuator assembly 52. For example, a handle, switch, button, or the like, may be provided to permit a user to move the collar 150 between the first position and the second position.

Figure 7:
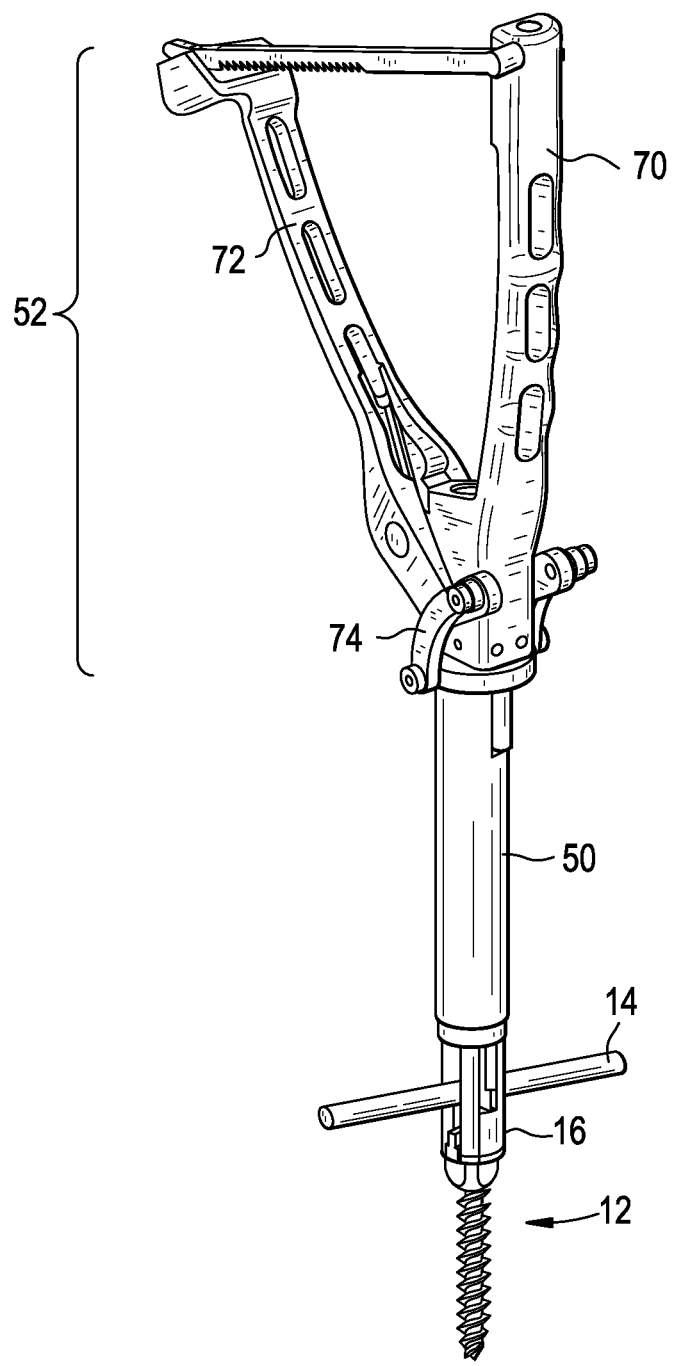
FIG. 7 is a perspective view of the system of FIG. 1, illustrating the instrument connected to the anchor extension and the reduction member in a proximal position.
Figure 8:
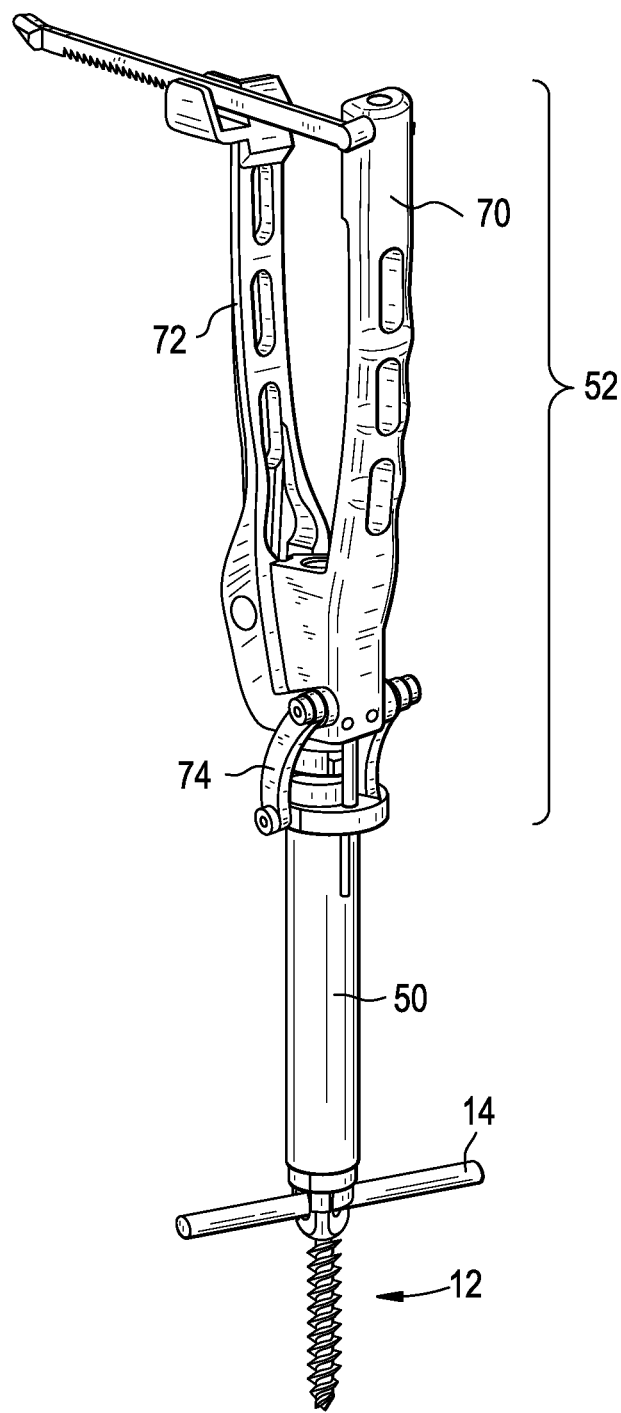
FIG. 8 is a perspective view of the system of FIG. 1, illustrating the instrument connected to the anchor extension and the reduction member in a distal position reducing the spinal rod relative to the bone anchor.

In accordance with one exemplary method of reducing a spinal rod relative to a bone anchor connected to an anchor extension, the reduction member 50 of the exemplary instrument 18 may be positioned about an anchor extension 16 connected to a bone anchor 12. The connection mechanism 54 of the instrument 10, for example the collar 150, may be moved from the released (second) position, illustrated in FIG. 3, to a connected (first) position, illustrated in FIG. 5, to connect the actuator assembly 52 of the instrument 18 to the anchor extension 16, as illustrated in FIG. 7. The actuator assembly 52 may be operated to move the reduction member 50 distally relative to the anchor extension 16 along the longitudinal axis 33 of the anchor extension 16 and to engage and move a spinal rod 14 into the U-shaped slot 28 of the rod receiver member 22 of the bone anchor 12. For example, the second handle 72 of the actuator assembly 52 may be moved toward the first handle 70 to cause the linkage 74 to move the reduction member 50 distally, as illustrated in FIG. 8. Once the spinal rod 14 is properly seated within the U-shaped slot 28 of the rod receiver member 22 of the bone anchor 12, a closure mechanism may be delivered to the bone anchor 12 through the central passage 82 of the distal base 76 of the first handle 70 and through the central passage of the anchor extension 16. The closure mechanism may be secured to the bone anchor 12 to capture the spinal rod 14 within the U-shaped slot 28. The connection mechanism 54, for example the collar 150 may be moved from the connected (first) position, illustrated in FIG. 5, to the released position, illustrated in FIG. 3, to permit disconnection of the actuator assembly 52 from the anchor extension 16. The actuator assembly 52 may be removed from the anchor extension 16 and the reduction member 50 may be removed from about the anchor extension 16.

In procedures in which multiple bone anchors are employed, the reduction member 50 of the instrument 18 may be positioned about a second anchor extension connected to a second bone anchor and the connection mechanism 54 of the instrument 18 may be connected to the second anchor extension in the manner of first anchor extension. The actuator assembly 52 may be operated to move the reduction member 50 distally relative to the second anchor extension along the longitudinal axis of the anchor extension and to engage and move the spinal rod 14 into the U-shaped slot of the receiver member of the second bone anchor. Once the spinal rod 14 is secured to the second bone anchor, his method may be employed for additional bone anchors and additional spinal rods.

Figure 9:
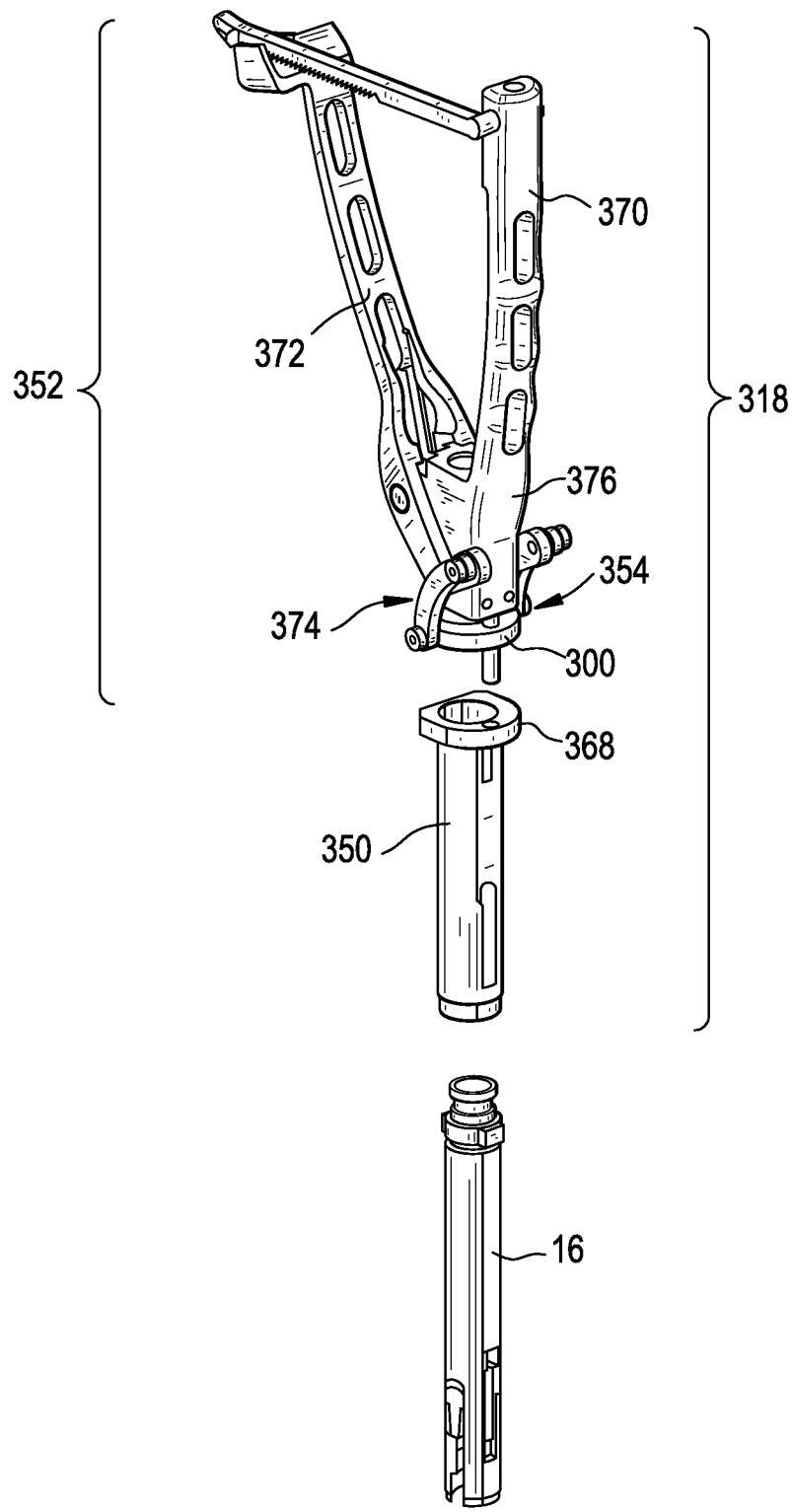
FIG. 9 is an exploded view of another embodiment of a spinal system, illustrating an anchor extension and an instrument for reducing the spinal rod relative to the bone anchor.

FIG. 9 illustrates in alternative embodiment of an instrument 318 for reduction of a spinal rod in which the actuator assembly 352 of the instrument 318 is not connected to the reduction member 350 by the linkage 374. Instead, the linkage 374 connects the second handle 372 to a distal flange 300 positioned distal to the distal base 376 of the first handle 370. The distal surface of the flange 300 engages the proximal surface of the collar 368 of the reduction member 350. Operation of the actuator assembly 352 by, for example, moving the second handle 372 toward the first handle 370, causes the linkage 374 to move the flange 300 distally which in turn acts upon the collar 368 of the reduction member 350 to move the reduction member 350. By separating the actuator assembly 352 from the reduction member 350, the reduction member 350 may be positioned about the anchor extension 16 independent of the actuator assembly 352 and connection mechanism 354. In certain systems, multiple reduction members 350, including, for example, reduction members 350 of vary sizes (e.g., diameters and lengths) may be provided. Such reduction members 350 may be used with a single actuator assembly 352 and connection mechanism 354.

Figure 10:
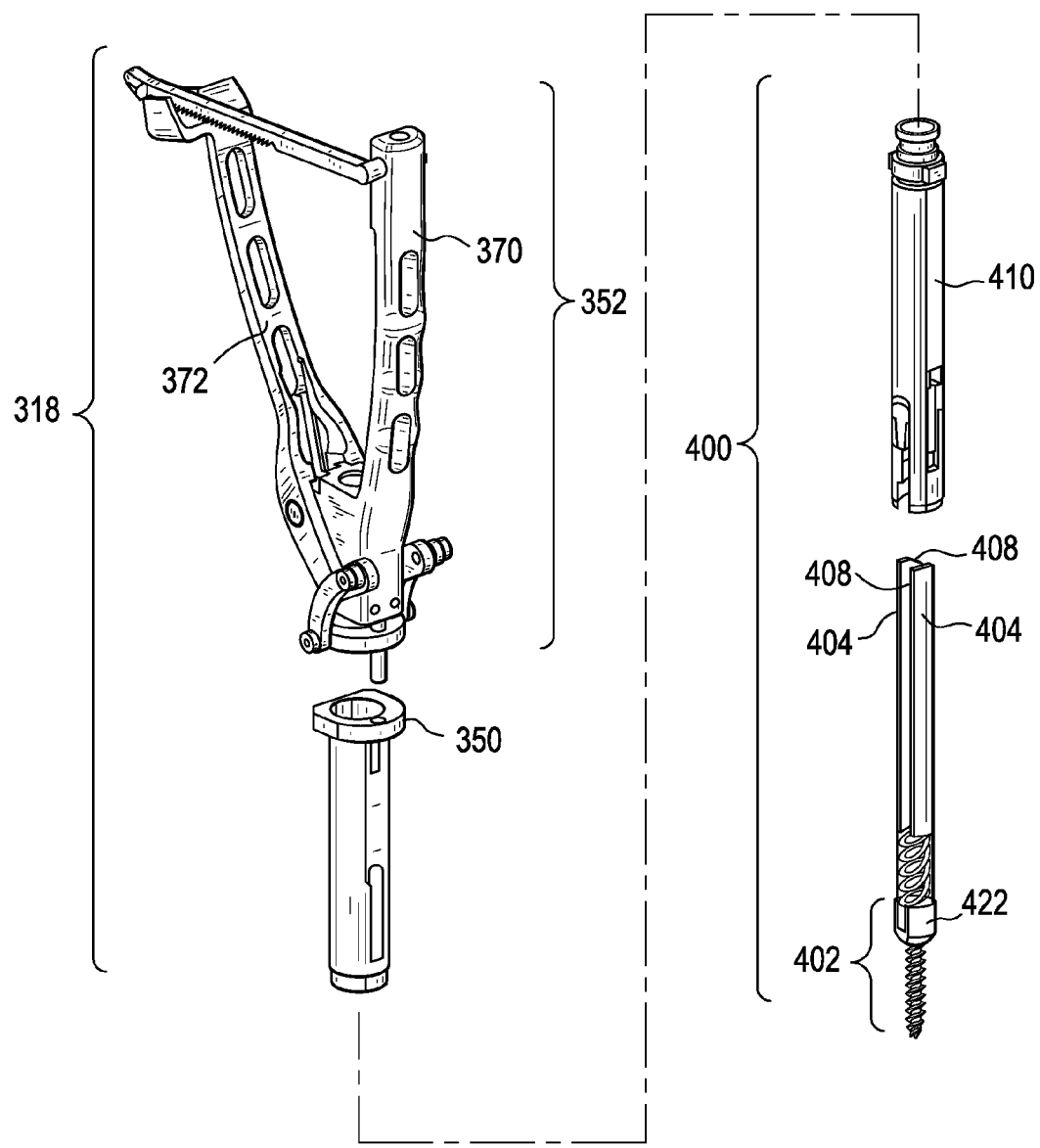
FIG. 10 is an exploded view of another embodiment of a spinal system including a bone anchor, a spinal rod, an anchor extension, and an instrument for reducing the spinal rod relative to the bone anchor.
Figure 11:
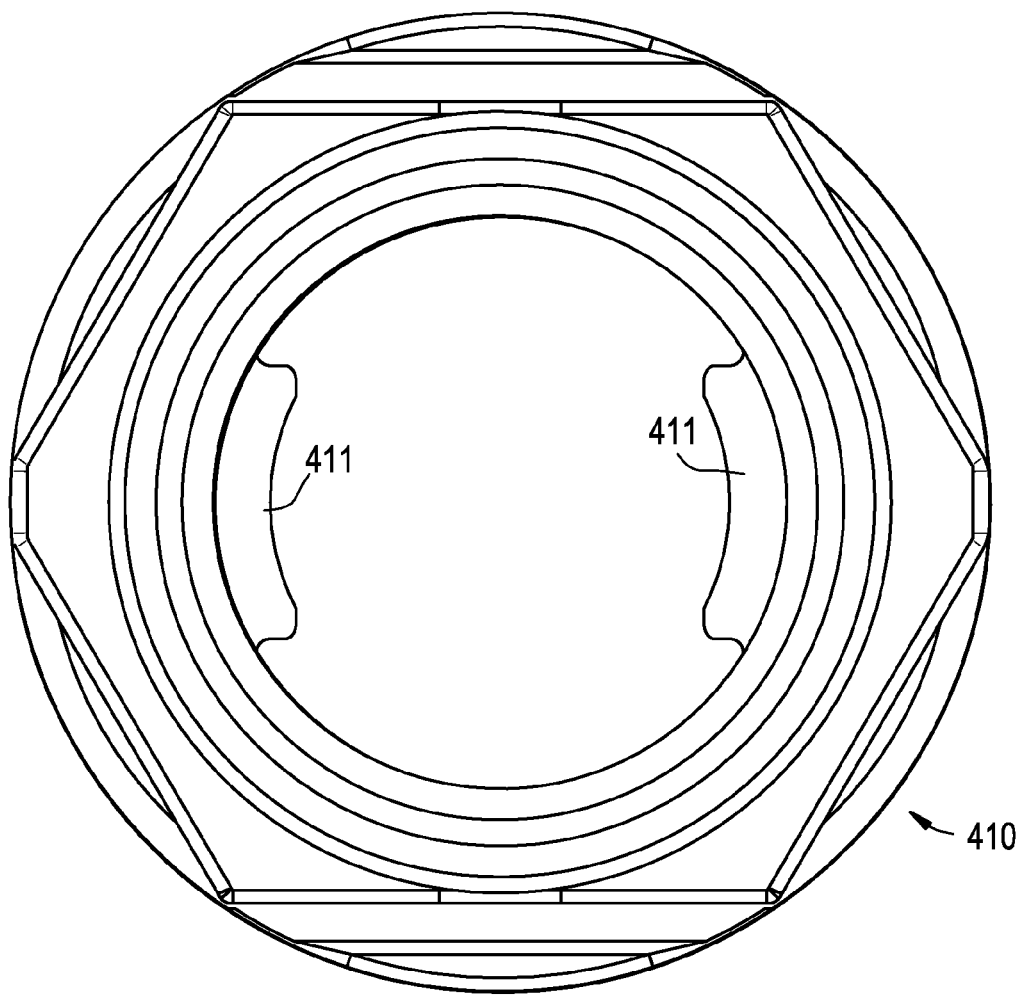
FIG. 11 is a top view of the anchor extension of the system of FIG. 10.

The rod reduction instruments disclosed herein may be used with anchor extensions of various types. For example, FIGS. 10 and 11 illustrate an anchor extension system 400 including a bone anchor 402 having a pair of spaced apart break-off extensions 404 extending proximally from the rod receiver member 422 of the bone anchor 402. Exemplary break-off extension bone anchors are disclosed in U.S. Patent Application Publication Nos. 2008/0119849, 2008/0300638, and 2009/0228052, each of which is hereby incorporated herein by reference. Each break-off extension 404 includes an internal thread at the distal end 406 thereof for engagement with the closure mechanism of the bone anchor. Each break-off extension 404 connects to the receiver member 422 of bone anchor 402 at a reduced thickness region that facilitates separation of the extension 404 from bone anchor 402 after the spinal rod is secured to the bone anchor. The break off extensions 404 are spaced apart to provide a pair of slots 408 for receiving the spinal rod. The slots 408 open at the distal end and communicate with the U-shaped rod slot formed in the receiver member 422 of the bone anchor 422. The slots 408 extend proximally from the connection with the receiver member 422 and, in the illustrated embodiment, are uninterrupted along the length of the extensions 404, although in alternative embodiments, one or more connection members may connect the extensions and thereby interrupt the slots 408. A second extension 410, analogous in construction to anchor extension 16 described above, may be positioned about the extensions 404 to stabilize and inhibit premature separation of the extensions 404 from the bone anchor 402. In this regard, the second extension 410 may include two opposed projections 411 sized and shaped to fit within the slots 408 between the extensions 404 and thereby inhibit motion of the extensions 404 toward one another. A spinal rod reduction instrument, such as instrument 18 or instrument 318 (illustrated), may be connected to the second extension 410 in the manner described above.

Alternatively, the extensions 404 may be provided with a feature, such as a groove or the like, to permit direct connection of the spinal rod reduction instrument, such as instrument 18 or instrument 318, to the extensions 404 thereby eliminating the need for the second extension 410.

While the instruments and methods of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

What is claimed is:

1. A spinal system comprising,
a bone anchor having a bone screw connected to a rod receiving member, the rod receiving member having a distal base and two spaced apart arms extending proximally from the base and forming a U-shaped slot for receiving a spinal rod,
an anchor extension having a distal end connectable to the receiver member, a proximal end, and a longitudinal axis extending between the proximal end and the distal end, the proximal end of the anchor extension including a flange having a diameter, and
a spinal rod reduction instrument comprising,
a reduction member positioned about the anchor extension and movable axially along the longitudinal axis of the anchor extension,
an actuator assembly connected to the reduction member and operable to move the reduction member distally relative to the anchor extension along the longitudinal axis of the anchor extension, and
a connection mechanism for removable and replaceable connection of the actuator assembly to the proximal end of the anchor extension, the connection mechanism being adjustable between a first position in which the connection mechanism connects the actuator assembly to the proximal end of the anchor extension and a second position in which the connection mechanism and the actuator assembly are released from the anchor extension, the connection mechanism comprising a collar having a slot positionable about the proximal end of the anchor extension, the slot having a first end with a reduced width and a second end with an increased width, the reduced width of the first end of the slot being less than the diameter of the flange on the proximal end of the anchor extension to permit connection of the collar to the anchor extension, and the increased width of the second end of the slot being greater than the diameter of the flange to permit removal of the collar from the anchor extension, the collar being adjustable in a direction transverse to the longitudinal axis of the anchor extension to move the collar between the first position and the second position, whereby, upon connection of the actuator assembly to the anchor extension by the connection mechanism, operation of the actuator assembly moves the reduction member distally to engage and move a spinal rod into the U-shaped slot of receiver member of the bone anchor, whereby when the collar is in the first position, the first end of the slot is positioned about the proximal end of the anchor extension distal to the flange and during operation of the actuator assembly the collar engages the flange to connect the actuator assembly to the anchor extension, and whereby when the collar is in the second position, the second end of the slot is positioned about the proximal end of the anchor extension to permit removal of the collar from the anchor extension by moving the collar proximally over the flange.

2. The spinal system of claim 1, wherein the collar is biased to the first position.

3. The spinal system of claim 1, wherein operation of the actuator assembly causes the collar to move to the first position.

4. The spinal system of claim 3, wherein the actuator assembly includes a first handle and a second handle pivotably connected to the first handle, a portion of the second handle engaging the collar, wherein movement of the second handle toward the first handle causes the collar to move to the first position.

5. The spinal system of claim 1, wherein the collar is movable between the first position and the second position independent of the operation of the actuator assembly.

6. The spinal system of claim 1, wherein the actuator assembly comprises
a first handle,
a second handle pivotally connected to the first handle, and
a linkage connecting the second handle to the reduction member,
whereby pivoting of the second handle toward the first handle causes the reduction member to move distally.

7. The spinal system of claim 1, wherein the actuator assembly includes an alignment member connecting the actuator assembly to the reduction member and preventing rotation of the actuator assembly relative to the reduction member.

8. The spinal system of claim 1, wherein the actuator assembly comprises
a first handle,
a second handle pivotally connected to the first handle,
a reduction flange distal to the first and second handles, and
a linkage connecting the second handle to the reduction flange,
whereby pivoting of the second handle toward the first handle causes the reduction flange to move distally and engage the reduction member to move the reduction member distally.

9. The spinal system of claim 1, wherein the reduction member is a cylindrical sleeve having a proximal end and a distal end.

10. The spinal system of claim 9, wherein the distal end of the sleeve includes a first pair of diametrically opposed arcuate cut-outs to engage the rod.

11. The spinal system of claim 10, wherein the distal end of the sleeve includes a second pair of diametrically opposed arcuate cut-outs, each of the second pair of cut-outs being offset 90 degrees from one of the cut-outs of the first pair.

12. The spinal system of claim 1, wherein the anchor extension comprises a cylindrical sleeve having a distal end connectable to the arms of the receiver member of the bone anchor.

13. The spinal system of claim 12, wherein the sleeve includes a pair of opposed slots, each slot being open at the distal end of the sleeve and extending proximally from the distal end of the sleeve.

14. The system of claim 1, wherein the anchor extension comprises a pair of break-off extensions, each extension having a distal end connected to one of the arms of the receiver member of the bone anchor, the distal end each extension configured to permit selective separation from one of the arms.

15. The system of claim 14, wherein the reduction member is a cylindrical sleeve, the sleeve including an inner wall haveing opposing projections sized and spaced to fit between the extensions when the sleeve is positioned about the extensions.

16. An instrument for reducing a spinal rod relative to a bone anchor connected to an anchor extension, the instrument comprising,
a reduction member sized and shaped to be positioned about an anchor extension connected to a bone anchor,
an actuator assembly connected to the reduction member and operable to move the reduction member distally relative to the anchor extension along a longitudinal axis of the anchor extension, and
a connection mechanism for removable and replaceable connection of the actuator assembly to a proximal end of the anchor extension, the connection mechanism being adjustable between a first position in which the connection mechanism connects the actuator assembly to the proximal end of the anchor extension and a second position in which the connection mechanism and the actuator assembly are released from the anchor extension, the connection mechanism comprising a collar having a slot positionable about the proximal end of the anchor extension, the slot having a first end with a reduced width and a second end with an increased width, the reduced width of the first end of the slot being less than a diameter of a flange at the proximal end of the anchor extension to permit connection of the collar to the anchor extension, and the increased width of the second end of the slot being greater than the diameter of the flange to permit removal of the collar from the anchor extension, the collar being adjustable in a direction transverse to the longitudinal axis of the anchor extension to move the collar between the first position and the second position, whereby, upon connection of the actuator assembly to the anchor extension by the connection mechanism, operation of the actuator assembly moves the reduction member distally to engage and move a spinal rod into a U-shaped slot of a rod receiver member of the bone anchor, whereby, when the collar is in the first position, the first end of the slot is positioned about the proximal end of the anchor extension distal to the flange and during operation of the actuator assembly the collar engages the flange to connect the actuator assembly to the anchor extension, whereby, when the collar is in the second position, the second end of the slot is positioned about the proximal end of the anchor extension to permit removal of the collar from the anchor extension by moving the collar proximally over the flange.

17. The instrument of claim 16, wherein the collar is biased to the first position.

18. The instrument of claim 16, wherein operation of the actuator assembly causes the collar to move to the first position.

19. The instrument of claim 18, wherein the actuator assembly includes a first handle and a second handle pivotably connected to the first handle, a portion of the second handle engaging the collar, wherein movement of the second handle toward the first handle causes the collar to move to the first position.

20. The instrument of claim 16, wherein the collar is movable between the first position and the second position independent of the operation of the actuator assembly.

21. The instrument of claim 16, wherein the actuator assembly comprises
a first handle,
a second handle pivotally connected to the first handle, and
a linkage connecting the second handle to the reduction member,
whereby pivoting of the second handle toward the first handle causes the reduction member to move distally.

22. The instrument of claim 16, wherein the actuator assembly includes an alignment member connecting the actuator assembly to the reduction member and preventing rotation of the actuator assembly relative to the reduction member.

23. The instrument of claim 16, wherein the actuator assembly comprises
a first handle,
a second handle pivotally connected to the first handle,
a reduction flange distal to the first and second handles, and
a linkage connecting the second handle to the reduction flange,
whereby pivoting of the second handle toward the first handle causes the reduction flange to move distally and engage the reduction member to move the reduction member distally.

24. The instrument of claim 16, wherein the reduction member is a cylindrical sleeve having a proximal end and a distal end.

25. The instrument of claim 24, wherein the distal end of the sleeve includes a first pair of diametrically opposed arcuate cut-outs to engage the rod.

* * * * *